United States Patent [19]

Lefkowitz

[11] Patent Number: 4,676,752
[45] Date of Patent: Jun. 30, 1987

[54] GINGIVAL BREATH DEODORIZER AND BITE GUARD

[76] Inventor: Jeffrey Lefkowitz, 833 W. 46 St., Miami Beach, Fla. 33140

[21] Appl. No.: 809,253

[22] Filed: Dec. 16, 1985

[51] Int. Cl.$^4$ .............................................. A61C 15/00
[52] U.S. Cl. .................................................. 433/229
[58] Field of Search .................. 433/229, 184, 215, 80

[56] References Cited

U.S. PATENT DOCUMENTS

| 3,600,807 | 8/1971 | Sipos | 433/229 |
| 4,106,501 | 8/1978 | Ozbey et al. | 433/80 |
| 4,583,982 | 4/1986 | Vlock | 433/80 |

FOREIGN PATENT DOCUMENTS 393629  11/1965  Switzerland .......................... 433/80

*Primary Examiner*—Robert Peshock
*Attorney, Agent, or Firm*—Victor F. Volk

[57] ABSTRACT

The invention relates to an intraoral dispensing apparatus for rendering the breath of a person aromatically pleasant. A vesicle is disposed about and in contact with the gingiva or dental gums and contains a supply of breath deodorizing or sweetening solution, which may include medications. A valve is provided for selectively dispensing solution as desired by the user, and is activated by finger pressure on the outside of the cheek. The dispensing valve operates only selectively to release solution to avoid flavor contamination of food when eating. Filling means are provided to recharge the vesicle. An alternative model is adaptable for use with dentures and can comprise a vesicle formed from a single layer of material attached about its periphery on the gingival surface of the denture. Other alternatives include combination of the foregoing with a bite opener, temporo-mandibular joint syndrome corrector, herbst appliance, etc.

3 Claims, 9 Drawing Figures

U.S. Patent  Jun. 30, 1987  4,676,752
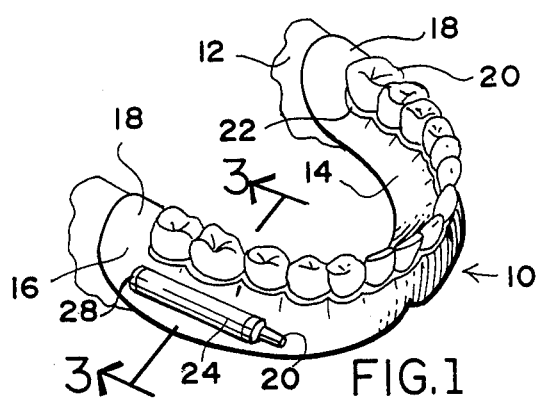
FIG.1
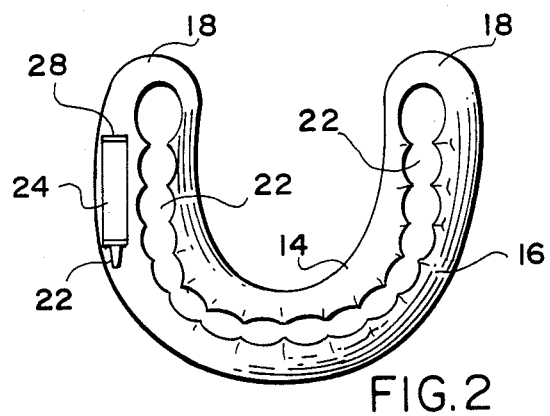
FIG.2
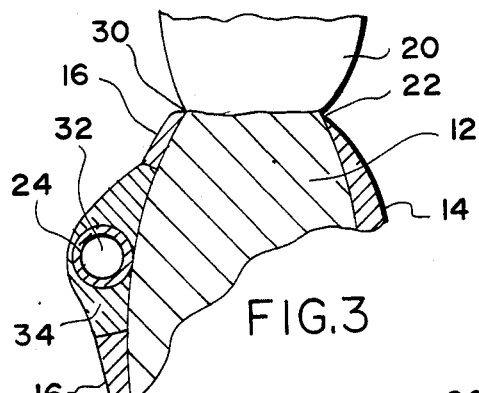
FIG.3
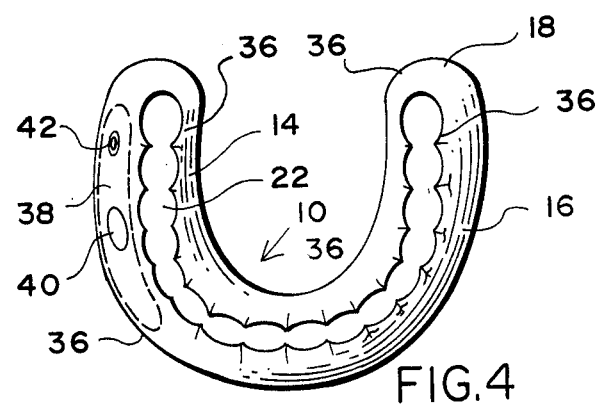
FIG.4
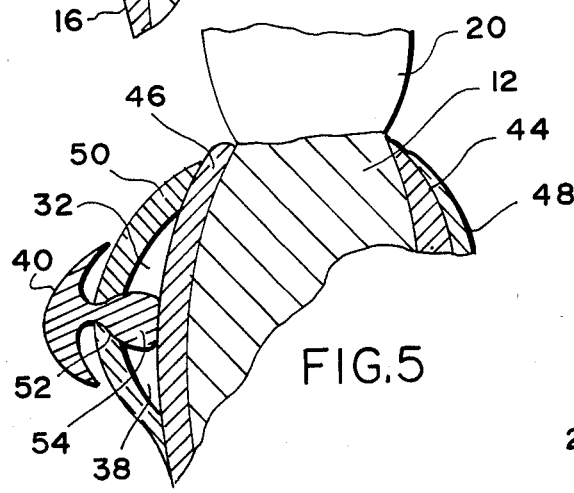
FIG.5
FIG.6
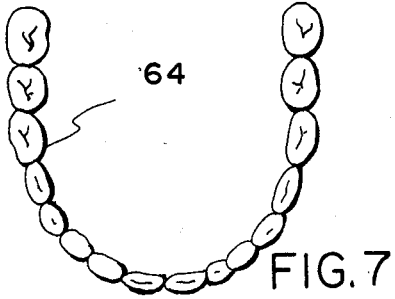
FIG.7
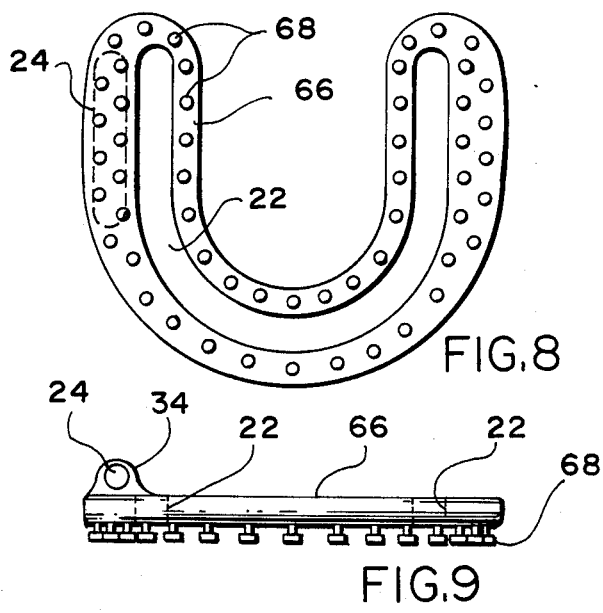
FIG.8
FIG.9

GINGIVAL BREATH DEODORIZER AND BITE GUARD

FIELD OF THE INVENTION

This invention relates to the field of dental appliances and, more particularly, comprises an intraoral dispensing apparatus disposed in proximity to the gingiva or dental gum and is selectively operable by the user.

BACKGROUND OF THE INVENTION

Most of us are well acquainted with "bad breath". It is generally offensive to those who encounter it, frequently when the person suffering from same is unaware of the problem. Such bad breath arises from various causes in the complex chemistry of the mouth and may include disease of the gingiva, uncontrolled plaque formation and even stomach related disorders.

Moreover, as the population increases, the number of people suffering with the social stigma of bad breath also increases. The need for a more efficient and effective oral deodorizer is accordingly more acute now than ever before. The simple use of various forms of mouthwash, lozenges and the like will never represent a complete answer because of the short period of the effectiveness that is found with such remedies. Other therapeutic devices that have appeared in the past have been very limited for practical use. It is clear that there is a need for an oral device that is effective for a more sustained period, easy to replenish, does not interfere with speaking, eating, or drinking, and is preferably not visible to others during the course of day-to-day activities. It is also highly desirable that a such a therapeutic device be designed and constructed such that it responds only selectively and does not continue to dispense when eating or drinking, the effect of which will be to impart a foreign flavor to food or drink. Previously known devices include U.S. Pat. No. 3,600,807 issued to Sipos, et al., which teaches a hollowed out tooth of a denture, in which an absorbent material is saturated with a deodorant solution. The solution is slowly, but continuously, released in the mouth until the same is exhausted, at which time it is recharged with additional solution. However, this device, unlike the present invention, releases its solution continuously which has the effect of flavor contamination while eating or drinking. In contrast, the present invention provides a selectively controllable dispensing valve that allows release of the deodorant solution only when the valve is activated by the user.

Another prior art device is Kasdin, et al., U.S. Pat. No. 3,503,127, which teaches a hollowed out denture for use with a pill or concentrate of a chemical sweetening agent that dissolves slowly and flows through openings in a cover plate. As with the Sipos device, this is an uncontrolled and continuous release, and the user, at mealtime, ends up with peppermint flavored mashed potatoes. The present invention effectively avoids such flavor contamination. Also, the present invention is not confined to denture wearers as with both of the preceding references, but may be used by persons having all or many of their natural teeth, but who also need a breath sweetening aid for various reasons.

U.S. Pat. No. 3,153,855 by Holland, et al. also teaches a hollowed out artificial tooth with an internal cavity to contain a sweetening solution. This reference discloses a small rotatable ball with a slightly roughened surface utilized to carry the solution into the mouth whenever the ball is rotated. This represents a better method than that employed in the foregoing references, but the difficulty of chemical sweetener mixing with food or drink is not resolved, because normal contact of the dispensing ball with food or other movement within the mouth while eating or drinking will rotate the ball and dispense solution into the food or beverage. In contrast, the present invention only releases solution when the dispensing valve is selectively operated, the same generally being constructed with a flange on the valve stem which is so shaped so as to allow food particles to pass behind the flange as well in front of it, thereby avoiding accidental dispensing while masticating food.

U.S. Pat. No. 3,808,686 by Tauman, et al. teaches a method of combatting foul breath by the application of a hydrophilic polymer to the top surface of an upper dental plate. The polymer contains a flavoring agent to combat breath odors. This reference neither teaches nor suggests the structure of the present invention.

Another artificial tooth that is hollowed out is disclosed by Baumgardner, U.S. Pat. No. 2,574,810. In this case, the purpose is to provide a shock absorbing device to imitate the natural tooth action in the alveolar socket. It also does not teach or suggest the structure of the present invention.

Other less relevant references are known and made a matter of record elsewhere, but a review of all of the prior art known to the inventor indicates that neither the present invention structure nor the selective release of oral deodorizer made possible by such structure are anticipated or suggested by such prior art.

SUMMARY OF THE INVENTION

Bearing in mind the foregoing, it is a principal object of this invention to provide a gingival breath deodorizer comprising an intraoral dispensing apparatus which dispenses only at the selective option of the user.

It is a further object of the invention to provide a substantially leak proof dispensing valve to avoid continuous release of breath deodorizing or sweetening solution into the mouth thus eliminating flavor contamination of food or beverages while the inventive apparatus is retained in the mouth of the user.

It is a primary object of the invention to provide an intraoral breath deodorizing dispensing apparatus that may be used with natural teeth, natural teeth and bridgework, or with full or partial dentures.

An important additional object of the invention is to provide a custom fitted dispenser that conforms precisely to the shape of the inside of the mouth and further provides a comfortable device that is agreeable to use.

A collateral object of the invention is to provide a novel blister type of vesicle which may be mounted on the surface of a denture and may comprise a single layer having a filling aperture and a selective dispensing valve sealingly attached to said surface.

A still further object of the invention is to provide a dispenser having a plurality of vesicles with separate dispensing valves and separate filling apertures for each vesicle, allowing the dispensing of different solutions within the mouth.

One more object of the invention is to provide an intraoral dispensing apparatus containing a supply of breath deodorizing solution, possibly including medications, having a greater capacity than that furnished by prior art devices.

A still further object of the invention includes combination of the above-described structure with a biteguard, bite opener, temporo-mandibular joint syndrome corrector, herbst appliance and the like.

Other objects and advantages will be readily apparent to those skilled in the art.

In accordance with the invention, there is provided an intraoral dispensing apparatus for rendering the breath of a person aromatically pleasant. A vesicle is disposed about and in contact with the gingiva or dental gums and contains a supply of breath deodorizing or sweetening solution, which may include medications. A valve is provided for selectively dispensing solution as desired by the user, and is activated by finger pressure on the outside of the cheek. The dispensing valve operates only selectively to release solution to avoid flavor contamination of food when eating. Filling means are provided to recharge the vesicle. An alternative model is adaptable for use with dentures and can comprise a vesicle formed from a single layer of material attached about its periphery on the gingival surface of the denture. Optionally, the inventive apparatus may be combined with a biteguard, bite opener, temporo-mandibular joint syndrome corrector, herbst appliance and the like, the structure of which is well known to the art.

In accordance with a further aspect of the invention, there is provided a new and unique method of manufacture as a natural consequence of the novelty of the inventive structure. Said method may comprise taking impression of patient, pouring of study models, vacuum forming a plastic sheet which may be of the order of 0.002 inches in thickness to the study model, placement of a preformed dispenser in the mucobuccal fold area. This preformed dispenser is provided with a filling aperture and a dispensing valve as above described. Alternatively, a spacing material such as clay may be placed in the mucobuccal fold area to form a reservoir. Referring to the principal method, however, a second ply of plastic can be vacuum formed in the manner described above for the first ply, then both plys are trimmed to remove the area thereof that covers the dentition and then a vesicle, preferably in the form of a bladder such as a fountain pen ink bladder is positioned in and flexibly attached to the outer ply. This is preferably accomplished by providing an opening in the outer ply for the same, and covering the same and attaching it to the outer ply with silicone which, when hardened, forms a flexible connection to the outer ply. The vesicle or bladder is preferably provided with two duckbill valves on either end, each being a one-way type of valve, the first constituting a dispensing valve and the other a filling aperture. It should be noted that silicone replaces the outer layer at the vesicle or bladder location because it is more flexible than the material that is vacuum formed from plastic sheet to form the above-described plys.

The present invention will be better understood upon reference to the following descriptions and the drawings in which:

BRIEF DESCRIPTION OF THE DRAWINGS

FIG. 1 is a perspective view of the preferred embodiment of the invention showing the same fitted over the gingiva of the lower jaw.

FIG. 2 is a top view of the preferred embodiment of the invention when the same has been removed from the gingiva of the lower jaw.

FIG. 3 shows an enlarged partial cross-section of the preferred embodiment of the invention taken along the line 3—3 of FIG. 1.

FIG. 4 shows a top view of a first alternative embodiment of the invention in a configuration similar to that shown in FIG. 2.

FIG. 5 is a view similar to that of FIG. 3 except showing a cross section of the first alternative embodiment shown in FIG. 4.

FIG. 6 is also a similar cross-sectional view illustrating the first alternative embodiment of the invention in use with a denture.

FIG. 7 shows a biteguard which is a natural by-product of the process of manufacturing either of the above-identified embodiments and which may be used simultaneously or independently of either embodiment.

FIG. 8 shows a bottom view of another alternative embodiment which is premanufactured for fitting by a customer.

FIG. 9 shows an end view of the embodiment of FIG. 8, and shows optional nodules or suction cups for retention purposes.

DETAILED DESCRIPTION

Shown in perspective view is the preferred embodiment of the inventive intraoral dispensing apparatus body 10 of the gingival breath deodorizer. It will be seen that the body 10 is disposed about and in close fitting proximity to the gingiva or dental gum 12, being comprised of a lingual portion 14 and a buccal portion 16 which portions are attached at 18 behind the last of the teeth 20. It will be seen that the intraoral dispensing apparatus body 10 is provided with a dentition perforation 22 allowing the teeth 20 to be exposed notwithstanding the close-fitting relationship of the inventive apparatus with the gingiva 12.

Attached to at least one buccal portion 16 of the intraoral dispensing apparatus body 10 is a bladder vesicle 24, which is attached thereto in a manner hereinafter described. The latter vesicle 24 is equipped with a dispensing valve 26 which may be of flexible duckbill construction and a filling aperture 28, which may also be of duckbill construction. Each may serve as a check valve such that dispensing valve 26 will only function in a dispensing mode and filling aperture 28 will only operate in a refill and not dispensing mode. Bladder vesicle 24 is intended to contain a quantity of breath deodorizing or sweetening liquid. Bladder vesicle 24 is flexible in construction so that pressure on the side thereof will cause the breath deodorizing liquid contents to be discharged from dispensing valve 26.

Turning now to FIG. 2, the preferred embodiment is seen in top view removed from the lower jaw on which it is illustrated in FIG. 1. The dentition perforation 22 can now be readily seen, as can the fact that the lingual portion 14 and buccal portion 16 are joined or attached only at 18. Also shown are vesicle bladder 24, dispensing valve 26, and filling aperture 28.

An important feature of the invention is that the same fits in the mouth of the user in a precise manner, i.e., that it conform to the exact shape of the interior of the mouth in the manner of a denture or orthodontic retainer, so as to be comfortable and secure. To ensure that a true and natural fit will be obtained, the invention contemplates a method for fabricating same including taking an impression of the patient, the pouring of study models, vacuum forming a plastic sheet to the study model, placement and attachment of a preformed dispenser in the mucobuccal fold area, preferably in the buccal portion 16 of the apparatus body 10. Of course, the dispensing valve 26 and filling aperture 28 may be of any appropriate design now known or hereafter developed, the inventor not meaning to limit the invention to the duckbill construction hereinabove described. Retention of the apparatus body 10 may be by means of an airtight seal, water or saliva between the invention and the gingiva, denture adhesive, or a mechanical undercut retention in close proximity to the teeth, or possibly partially covering a part of the exterior tooth surface adjacent the gingiva.

FIG. 3 illustrates an enlarged broken cross-section of the preferred embodiment, said cross-section taken along the line 3—3 of FIG. 1. A portion of the tooth 20 is seen above the gingiva 12. The lingual portion 14 and buccal portion 16 can be seen in close proximity to the gum line 30 therebetween forming the dentition perforation 22. Also seen in cross-section is the bladder vesicle 24 containing breath deodorizer 32. Bladder vesicle 24 is preferably held in place within an opening provided for same in buccal portion 16 by a flexible material. Preferably, bladder vesicle 24 is disposed within buccal portion 16 and then held in place with a prolastic silicone material 34. Obviously, other means of attachment of bladder vesicle 24 are fully within the contemplation of the invention.

In FIG. 3 it will be seen that the intraoral dispensing apparatus in its preferred embodiment as illustrated in FIGS. 1-3 is comprised of a single layer of material to which the bladder vesicle 24 has been attached. However, it is also fully within the contemplation of the invention that the same may be multiple layers of form-fitted material and in some instances a duplicate layer has been found advantageous for rigidity, retention, and/or wearing comfort.

FIG. 4 is also a top view, similar to FIG. 2, of an alternative embodiment. As will more clearly be seen in FIG. 5, the alternative embodiment of the inventive apparatus 10 is comprised of a plurality of layers which are nonetheless formed in a manner that is similar to the preferred embodiment. Thus, the alternative embodiment includes such features as the dentition perforation 22, the lingual portion 14, the buccal portion 16, connection between the latter two at 18, and the like. The plurality of layers are edge sealed by any appropriate means such as ultrasonic welding, glue, cement, silicone or the like at the periphery 36. It should be noted that the periphery 36 refers both to the more obvious extremity of the invention and also to portion thereof immediately adjacent to the dentition perforation 22. Disposed between two such layers is a blister vesicle 38 shown in phantom in FIG. 4. The blister vesicle is also provided for containing breath deodorizer 32 and is equipped with a dispensing valve 40 and filling aperture 42. It should be noted that the dispensing valve 40 is that of an umbrella valve as more fully described in regard to FIG. 5, but any operative valve now known or hereafter developed may serve and is fully within the contemplation of the invention. Thus, the duckbill construction of dispensing valve 26 and filling aperture 28 may be substituted for their counterparts illustrated in FIG. 4 without changing the spirit and scope of the invention.

Referring to FIG. 5, there is illustrated in a manner similar to FIG. 3 an enlarged partial cross sectional view except that what is shown in the first alternative embodiment described in connection with FIG. 4. Initially, it will be seen that the gingiva 12 is adjacent to the tooth 20. In proximity to the gingiva 12 are an inner lingual portion 44 of the alternative embodiment of the intraoral dispensing apparatus and inner buccal portion 46. The inner lingual portion 44 and inner buccal portion 46 are analogous to the lingual portion 14 and buccal portion 16 of the preferred embodiment. In close proximity thereto are the outer lingual portion 48 and outer buccal portion 50. The outer buccal portion 50 is sealingly disposed in respect to the inner buccal portion 46 about the perphery of blister vesicle 38 so as to contain therein breath deodorizer 32.

Penetrating outer buccal portion 50 is at least one opening 52, preferably of tapered diameter and having the minimum diameter exteriorly. When opening 52 is so tapered, it is fitted with dispensing valve 40 which is seen to be formed with an exterior surface similar to an umbrella and is otherwise described as an umbrella valve. The umbrella valve base 54 is seen to seat tightly against inner buccal portion 46 which in turn causes upper tapered surfaces of umbrella valve base 54 to seat tightly against the tapered sides of opening 52. However, umbrella valve base 54 is preferably fabricated from a compressible material such that when pressure is applied to the top of umbrella valve 40, umbrella valve base 54 compresses and permits opening 52 to discharge a modest quantity of breath deodorizer 32 therethrough. Upon release of pressure to umbrella valve 40, opening 52 is again sealed so there will be no discharge of breath deodorizer 32 to cause flavor contamination while eating or drinking.

A plurality of blister vesicles 38 may be disposed about the periphery of the invention, each being provided with separate dispensing valves 40 and filling apertures 42 such that the plurality of deodorizers, or deodorizer and medication can be released at will by the user. Incidentally, the pressure to be applied to umbrella valve 40 is achieved by pressure on the exterior of the cheek of the user in a manner which will be unobvious to the observer and that this can be accomplished for multiple blister vesicles by familiarity with the location of each valve. If food flows against umbrella valve 44, the effect will be to drag the valve outward and serve to further seal because the result is only to tighten the effect of the valve as a consequence of the direction of the tapered walls in opening 52. Eating or drinking activity does not cause unintentional discharge of breath deodorizer and consequent flavor contamination.

The plurality of layers associated with the first alternative embodiment described in connection with FIGS. 4 and 5 can also be utilized in connection with the preferred embodiment described in connection with FIGS. 1-3, and also with a second alternative embodiment described in regard to FIG. 6. Blister vesicle 38 and umbrella valve base 54 can be formed during the shaping of the inner and outer lingual and buccal portions of the invention by a clay spacer (not shown) which is removed prior to sealing outer buccal portion 50 to inner buccal portion 46 about the periphery of blister vesicle 38. Dispensing valves 40 will preferably be disposed in a buccal area of the invention rather than in the lingual area of the invention to prevent tongue irritation.

FIG. 6 illustrates a second alternative embodiment of the invention. In FIG. 6 the general configuration shown in FIG. 5 is illustrated, except that a single layer can be utilized. This is because tooth 56 and base 58 are actually portions of a denture to which the periphery 60 of denture blister vesicle 62 may be adhesively attached to contain breath deodorizer 32. Moreover, although not shown, an increased volumetric capacity of denture blister vesicle 62 is possible by grinding out a recess in base 58 adjacent to the denture blister vesicle 62. In other respects the second alternative embodiment illustrated in FIG. 6 is similar to that described in connection with FIG. 5 including the umbrella valve 40 opening 52 and umbrella valve base 54. In addition, the option described above in regard to the first alternative embodiment illustrated in FIGS. 4 and 5 regarding use of duckbill valve construction or any other operative-upon-command valve now known or hereafter developed may be substituted in the denture alternative embodiment as described in regard to FIG. 6.

It may be recalled from the prior descriptions that the method by which the intraoral dispensing apparatus is fabricated includes making a study mold of the mouth and then vacuum forming the invention thereabout. It should be noted that when multiple layers are used in combination with a preformed bladder or reservoir, the soft sided nature of the bladder would cause the same to collapse in the vacuum forming step of the method. Accordingly, a substantially stiffer sleeve is placed around the same to retain bladder shape during vacuum forming, and then removed to render the bladder again flexible in the final assembled product.

Further, it will be seen that when vacuum forming about the study mold, the same is accomplished about the teeth as well as the gums of the study mold. However, a portion of that is then removed by being cut therefrom to form the dentition perforation 22 as shown in FIGS. 1-4. The portion that is removed happens to be shaped precisely as the teeth of the user and may be retained for use as a biteguard for patients who are bruxers, i.e., those who grind their teeth, or for related use as a temporomandibular joint syndrome corrector, herbst appliance, etc. The biteguard appliance 64 resulting from the method of manufacture of the principal invention is illustrated in FIG. 7 and is a natural by-product as described of the method of manufacture of the present invention because it is simply cut from the same.

Turning now to FIG. 8, a still further alternative embodiment is illustrated in a bottom view. It is fabricated in a flat plastic sheet 66 which contains a dentition perforation 22, except that the latter is not conformed to actual tooth size, shape or placement because this embodiment is totally premanufactured and may be sold over the counter to the public and then taken by the patient and either conformed to the contours of his individual mouth by a reline by a dentist or by the customer himself utilizing reline material at home. The material is a malleable, flexible plastic described as moldable that is precut to fit any size mouth or comes in small, medium, and large sizes and that already contains a preformed dispenser such as the bladder vesicle 24 complete with inlet and outlet valves that is embedded between two plys of this plastic material 66. Of course, other bladder configurations may also be used, such as the blister vesicle 38 shown in FIG. 4. The customer may take a scissors and trim the material so as to better adapt it to his or her mouth. Then a dentist or the customer may take a plastic reline material or silicone material used for chairside relines such as Lang's ™ of Coe's ™ chairside reline material and adapt the invention to fit to the exact contours of the mouth. Once the reline material sets, it is trimmed and the invention then is held in place just as a denture is by adhesion or the use of adhesives. It is further held in place by the fact that, in the case of a plastic reline such as silicone, there are mechanical undercuts that lock in the device. Once trimmed, the device dispenses in the same manner as the other; that is by pressing on the single valve or on the dispenser itself by pressing on the cheek outside the dispenser. The dispenser portion is again placed in the mucobuccal fold area of the molar area up to the cuspid area.

The appearance of the premanufactured alternative embodiment can be no different than the previous embodiments other than the fact that it is flat and later conformed to the shape of the individual's mouth through the use of a chairside or home reline of soft reline material. Alternatively, it may have nodules 68 on its undersurface to aid in the retention of the reline material. Optionally, the nodules and reline material may be replaced with suction cups 68 which bear some resemblance to the nodules, but may provide all of the retention effects necessary, possibly eliminating the need for the reline material.

FIG. 9 shows the embodiment of FIG. 8 in an end view, illustrating its flat character prior to molding the same to the customer's mouth. Shown are the flat plastic sheet 66, bladder vesicle 24, which is held in place with prolastic silicone material 34, as in FIG. 3. Nodules or suction cups 68 are also shown. Dentition perforation 22 is shown in phantom.

It should be noted that all embodiments may have a single valve that has the quality of being both an inlet and outlet valve or there may be two one way valves, e.g., duckbills, placed at either end of the invention to serve as inlet and outlet valves.

With regard to all of the embodiments above described, it should be noted that various refill means are acceptable, but the preferred technique includes the use of a squeeze bottle refill dispenser containing the breath deodorizer 32 or appropriate medication. The connection to which it is selectively attached is filling aperture 28 or 42. Alternatively, a pressurized canister such as that currently used for refilling butane lighters may be used. Since the appearance and use of both such devices are extremely well known, the same are not illustrated.

It has been noted above that the invention may contain medication within one or more of the vesicles described in regard to the various embodiments. Additionally, however, a separate sealed reservoir can be removably attached at any convenient point to the apparatus illustrated and described above, the same being external thereto. It may be suitable for positioning by a finger or the tongue, so that it may be broken between the teeth. This separate sealed reservoir would presumably be for the purpose of emergency medication. An example is a capsule of nitroglycerin for cardiac patients. Obviously, removal attachment to the invention is so that the medication contained therein could be replaced after being used in a disposable type container.

Having described the presently preferred embodiment and alternative embodiments of the invention, the advantages and objects of the invention will be apparent to those skilled in the art and reasonable modifications thereto are fully contemplaced herein without departing from the true spirit of the invention. Accordingly, there are covered all alternatives, modifications and equivalents as may be included within the spirit and scope of the invention as defined solely by the appended claims.

What is claimed is:

1. A gingival breath deodorizer comprising:
a body molded for attachment and close fitting relationship to dental gingiva;
a vesicle disposed within the body, said vesicle being suitable for retention of fluid;
a selectively operable filling aperture in fluid communication with the vesicle;
said vesicle being defined by a premanufactured, substantially cylindrical, flexibly sided bladder attached to a buccal portion of the body and having at least one selectively operable orifice in fluid communication with the vesicle to serve as filling and dispensing means; and
a first orifice at a first end of the bladder service as the filling means and a second orifice at a second end of the bladder serving as the dispensing means, each orifice also acting as a check valve.

2. The deodorizer of claim 1 in which at least one orifice is a duckbill valve.

3. A gingival breath deodorizer comprising:
a body molded for attachment and close fitting relationship to dental gingiva;
a vesicle disposed within the body, said vesicle being suitable for retention of fluid; and
a selectively operable dispensing valve in fluid communication with the vesicle, said dispensing valve being comprised of:
a base fabricated of a resiliently compressible material;
upper tapered surfaces having a minimum diameter exteriorly;
a tapered diameter opening penetrating the body for fluid communication with the vesicle, walls of said opening being tapered with a minimum diameter exteriorly and said walls being shaped to mate with the upper tapered surfaces of the valve to effect sealing therebetween; and
an umbrella portion projecting about the opening and attached to the upper tapered surfaces, such that when pressure is manually applied to the umbrella portion, said pressure results in temporary compression at the base and temporary separation of the upper tapered surfaces from mating walls of the opening thereby allowing fluid retained in the vesicle to selectively escape.

* * * * *